US006642037B2

(12) United States Patent
Gordon et al.

(10) Patent No.: US 6,642,037 B2
(45) Date of Patent: Nov. 4, 2003

(54) PREPARATION OF ENZYMATICALLY ACTIVE SPONGES OR FOAMS FOR DETOXIFICATION OF HAZARDOUS COMPOUNDS

(75) Inventors: Richard K. Gordon, Potomac, MD (US); Bhupendra P. Doctor, Potomac, MD (US); Ashima Saxena, Fairfax, VA (US); Shawn R. Feaster, Damascus, MD (US); Donald Maxwell, Baltimore, MD (US); Michelle Ross, Edgewood, MD (US); David Lenz, Bel Air, MD (US); Keith Lejeune, Pittsburgh, PA (US); Alan Russell, Wexford, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/558,512

(22) Filed: Apr. 26, 2000

(65) Prior Publication Data

US 2003/0113902 A1 Jun. 19, 2003

Related U.S. Application Data

(60) Provisional application No. 60/130,987, filed on Apr. 26, 1999.

(51) Int. Cl.[7] .......................... C12N 11/04; C12N 11/08; C12S 9/00; C12S 13/00
(52) U.S. Cl. ................... 435/182; 435/180; 435/262.5
(58) Field of Search .............................. 435/262.5, 177, 435/174, 178, 180, 182

(56) References Cited

U.S. PATENT DOCUMENTS

| | | | |
|---|---|---|---|
| 4,324,858 A | 4/1982 | Goodson et al. | 435/20 |
| 4,411,989 A | 10/1983 | Grow | 435/20 |
| 4,677,019 A | 6/1987 | von Bluecher | 428/244 |
| 5,001,048 A | 3/1991 | Taylor et al. | 435/4 |
| 5,162,148 A | * 11/1992 | Boye et al. | 428/287 |
| 5,192,507 A | 3/1993 | Taylor et al. | 422/68.1 |

FOREIGN PATENT DOCUMENTS

WO    WO 87 00914 A    2/1987

OTHER PUBLICATIONS

Braatz, (1994) "Biocompatible Pllyurethane–Based Hydrogel" in Journal Biomaterials Applications, vol. 9.
Doctor, et al., (1991) "Enzymes as Pretreatment Drugs for Organophosphate Toxicity" Neuroscience & Biobehavioral Reviews, vol. 15, pp. 123–128.
Ember, (1997) "Detoxifying Nerve Agents" Chemical & Engineering News Sep. 15, 1997.
Gordon, et al., (1998) "Exploiting Immobilized Enzymes: Detoxification of Nerve Agents" Proceedings from the 6th CBW Protection Symposium, Stockholm, Sweden, May 1998.
Gordon et al., "Exploiting Immobilized Enzymes: Detoxification of Nerve Agents" in the Summary Digest of the 21st Army Science Conference, Jun. 15–17, 1998.
Gordon et al., (1997) "Potential Applications of Immobilized Cholinesterases: Tools for Protection, Decontamination, and Detection" in The ASA Newsletter 97–5, Issue No. 62.
Gordon et al., "Immobilized Enzymes—Selective and Specific Sensors for Organophosphate Chemical Toxins" a Proposal "White Paper" of Walter Reed Army Institute of Research.
Gordon et al., (1990) "Vasoactive Intestinal Polypeptides Induce Guinea–Pig Ileum Contraction by Causing Release of Endogenous Acetylcholine" Arch. Int. Pharmacodvn. 305, pp 14–24.
Havens et al., (1993) "Reusable Immobilized Enzyme/Polyurethane Sponge for Removal and Detoxification of Localized Organophosphate Pesticide Spills" Ind. Eng. Chem. Research 1993, 32, 2254–2258.
LeJeune et al., "Fighting Nerve Agent Chemical Weapons with Enzyme Technology", Ann NY Acad. Sci. (1998) 864:153–170.
LeJeune et al., (1996) "Covalent Binding of a Nerve Agent Hydrolyzing Enzyme Within Polyurethane Foams" in Biotechnology and Bioengineering, vol. 51, pp. 450–457.
LeJeune et al., (1996) "Covalent Linkage of Mammalian Cholinesterases Within Polyurethane Foams" Proceedings from the 1996 Medical Defense Bioscience Review.
Medlin, (1998) "Super Sponges" Environmental Health Perspectives, vol. 106, No. 4, pp. A182–184.
Russell, 1995 "Biocatalytic Nerve Agent Decontamination with Protein–Polymers" Univ. Pittsburgh Proposal to USAMRMC.

(List continued on next page.)

Primary Examiner—David M. Naff
(74) Attorney, Agent, or Firm—Elizabeth Arwine

(57) ABSTRACT

An enzymatically active reusable sponge or foam, capable of regeneration with oximes, made of a polymer such as polyurethane is prepared for detoxification of hazardous compounds such as organophosphorus and organosulfur compounds. The foam or sponge contains a plurality of enzymes including enzymes selected from acetylcholinesterase, butyrylcholinesterase, triesterase, pseudocholinesterase, organophosphate hydrase, phosphotriesterase, paraoxonase and organophosphorus and organosulfur hydrolyzing enzymes. The sponge or foam may additionally contain activated carbon and an enzyme reactivation compound. A kit can be formed containing the sponge or foam and the compound for enzyme reactivation. The enzymatically active foam or sponge may be prepared using a two chamber device where enzymes and prepolymer are passed from separate chambers into a static mixing stator and are subjected to low shear mixing and extrusion to form by the sponge or foam.

11 Claims, 20 Drawing Sheets

OTHER PUBLICATIONS

"Reactivation of Various OP Inhibited Immobilized (Sponge) FBS–AchE with HI–6" Table of data. Fax from Doctor, Dec. 21, 1995.

"Abstract: Covalent Linkage of Mammalian Cholinesterases and OP Hydrolyzing Enzymes Within Polyurethane Foams" Fax from Doctor to Russell Feb. 27, 1996 and fax from Madeya to Russell, Feb. 28, 1996.

Russell, Jun. 4, 1996 "White Paper: Biotechnology Versus Chemical Weapons: A Battle for the 21st Century. The Use of Stabilized Enzymes to Decontaminate and Demilitarize".

LeJeune, et al., "Dramatically Stabilized Phosphotriesterase—Polymers for Nerve Agent Degradation" Biotech & Bioeng. vol. 54, No. 2, Apr., 1997, PP 105–113.

"Abstract: Covalent Linkage of Mammalian Cholinesterases Within Polyurethane Foams" Fax from Doctor to Russell, Jun. 10, 1996. Submitted to the Proceedings of the 1996 Medical Defense Bioscience Review.

"Proceedings of the CB Medical Treatment Symposium: An Exploration of Present Capabilities and Future Requirements", Jul. 7–12, 1996 Spiez, Switzerland.

"Data Tables regarding polyurethane foam sponges" Fax from Doctor to LeJeune Apr. 17, 1997.

Solicitation DAA 005–97–I–1981, Contractor Russell for Synthesis work. Includes Univ. Pittsburgh data tables regarding synthesis.

Slide, notes indicate that prepared Sep. 22, 1997 and presented Oct. 15, 1997, Univ. Pittsburgh Seminar.

Slide, notes indicate that prepared Sep. 15, 1997 and presented Sep. 19, 1997, W.V.U. Grad Student Symposium.

Slide, notes indicate that prepared Nov. 21, 1996 and presented Apr. 1997, ACS Meeting.

LeJeune, 1997 "Biotechnology versus Chemical Weapons: Implementing Enzyme Technology in Bioremediation" Proposal to Department of Chemical Engineering, Carnegie Mellon Univ.

Russell, Nov. 13, 1997, "Biotechnology versus Chemical Weapons: Implementing Enzyme Technology in Decontamination/Demilitarization" Proposal to Edgewood Research, Development and Engineering Center.

Lejeune, et al., 1999 "Biocatalytic Nerve Agent Detoxification in Fire Fighting Foams" Chemical Abstracts, vol. 130, No. 19.

* cited by examiner

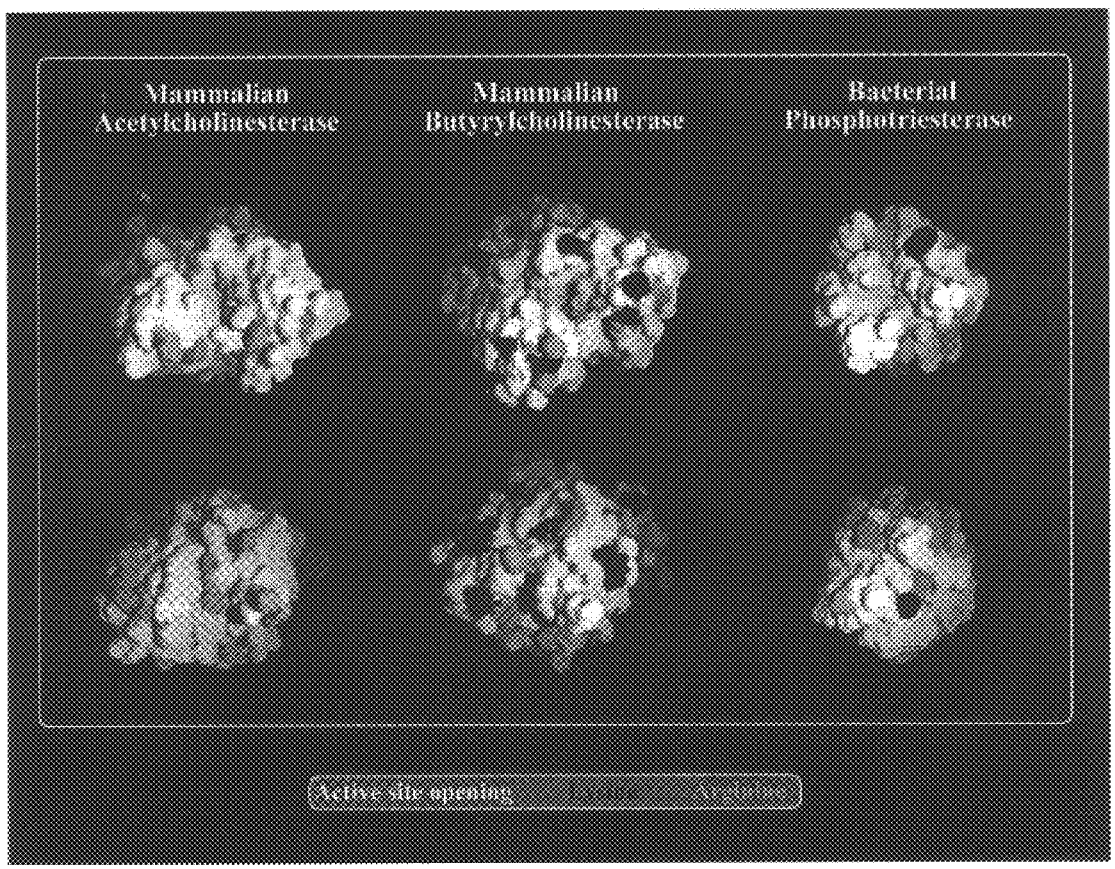

Figure 1A. Modeled surfaces of ChEs and triesterase. The top row shows a view of the front of the enzymes with the lip of the active site gorge outlined with a dotted line in the center. The bottom row shows the backside of the enzymes (180° rotation). The Lysine and Arginine residues on the surface, which are potential coupling sites to the polymer, are shaded dark in both the top and bottom row.

Figure 1B
Similarly, a model of the surface of laccase is shown with available residues to couple covalently to the prepolymer (top, front of enzyme; bottom, backside of enzyme).
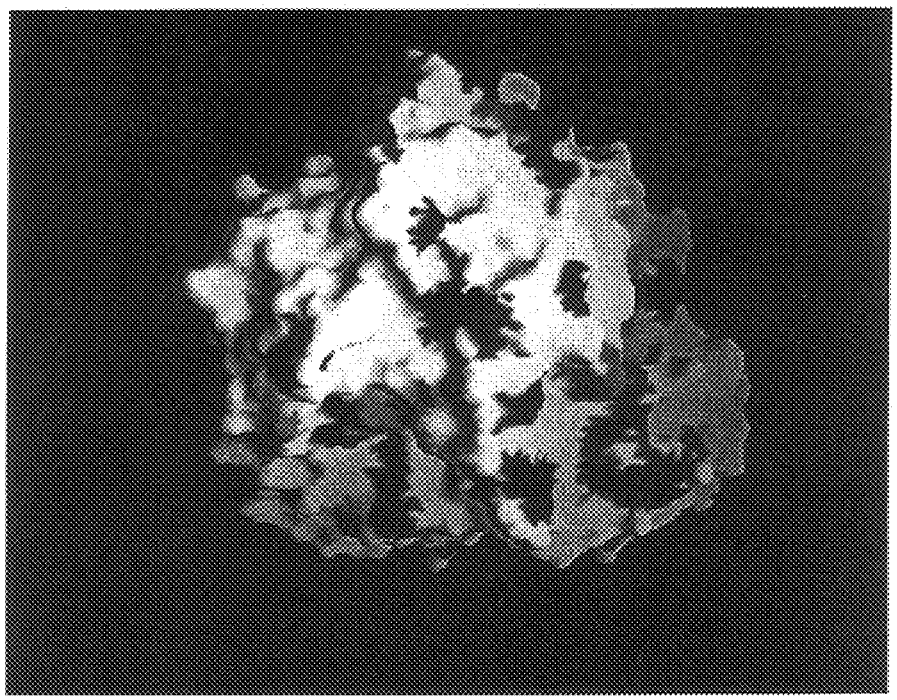
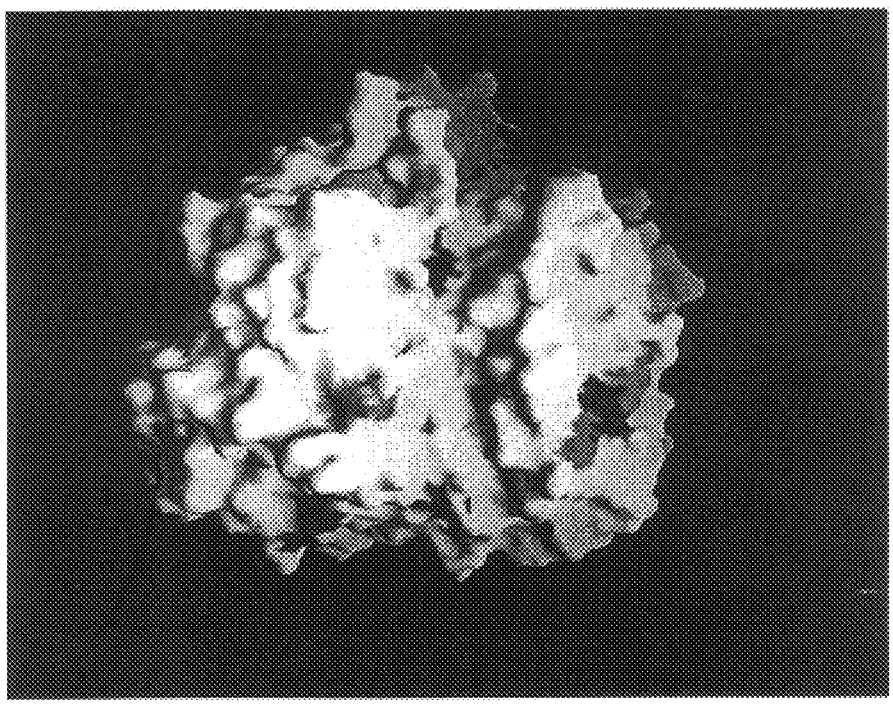

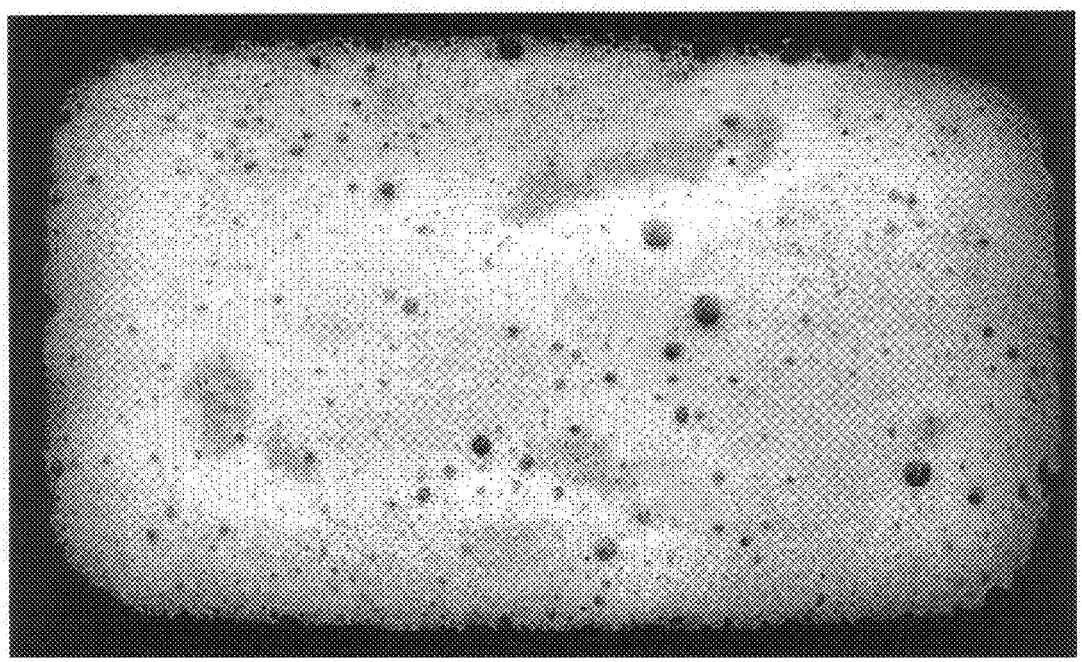
Figure 2. Final product: FBS-AChE sponge

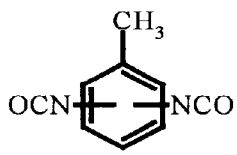
TDI prepolymer functional group
1. Aqueous Initiation of Polymerization
2. Amine Formation and $CO_2$ Evolution (foaming)
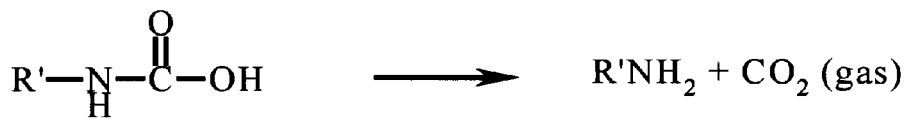
3. Prepolymer Crosslinking
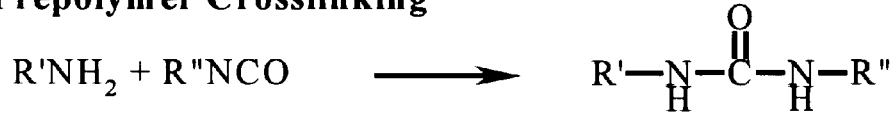
4. Covalent ChE Incorporation at Aliphatic Amino Group(s)
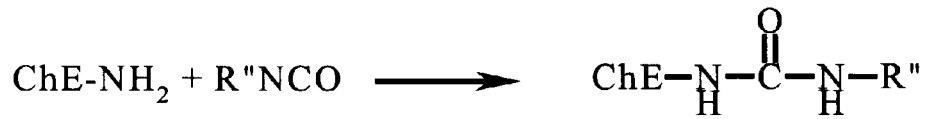
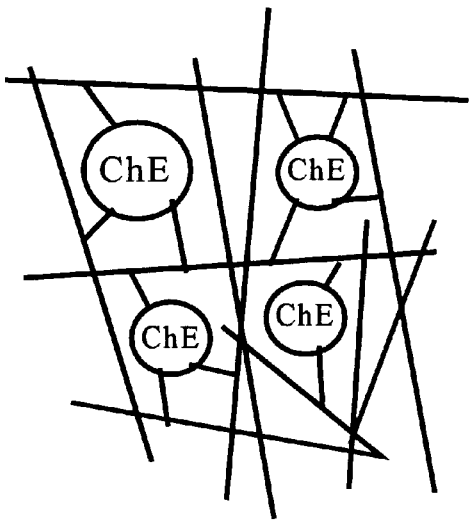
polyurethane crosslinked ChE
Figure 3

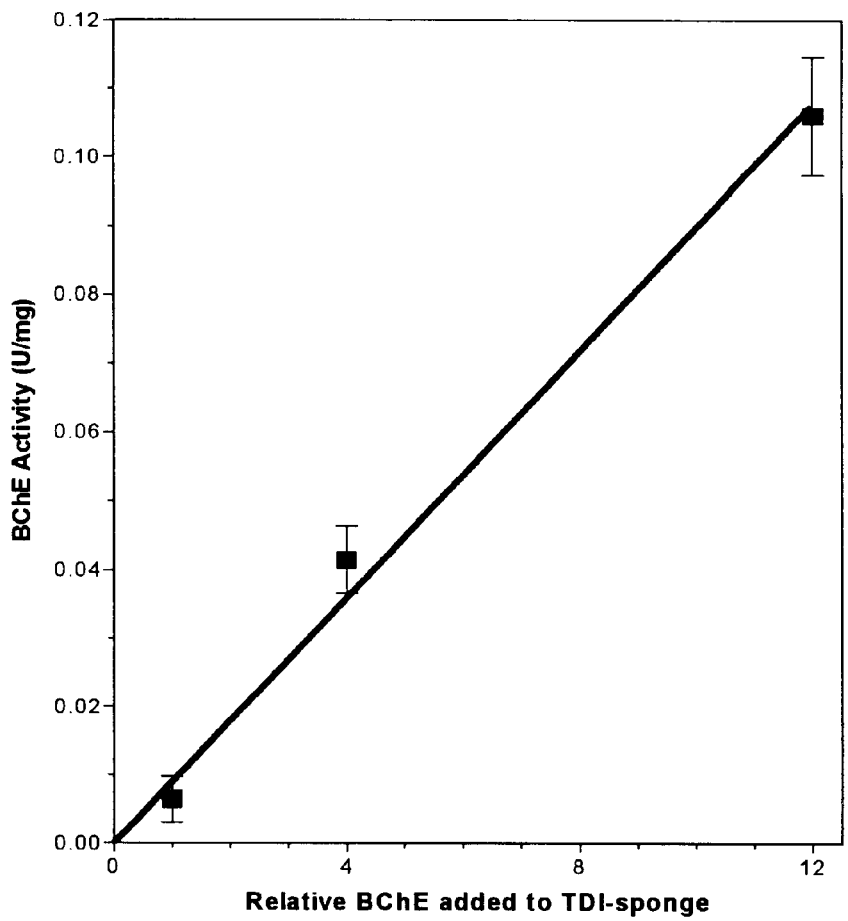
Figure 4. A linear correlation was observed between the amount of BChE added to the prepolymer during synthesis and the amount of BChE activity observed in the final sponge.

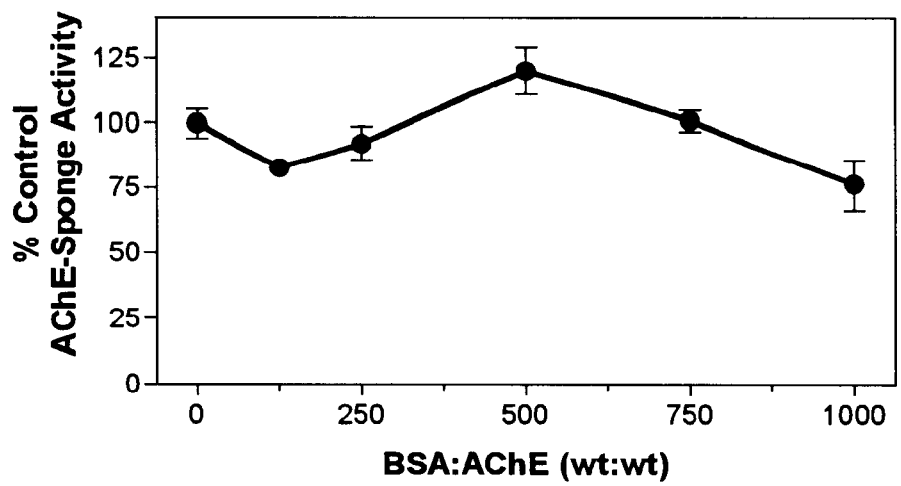
Figure 5. Increasing amounts of BSA were added during synthesis to a constant amount of AChE and TDI polymer

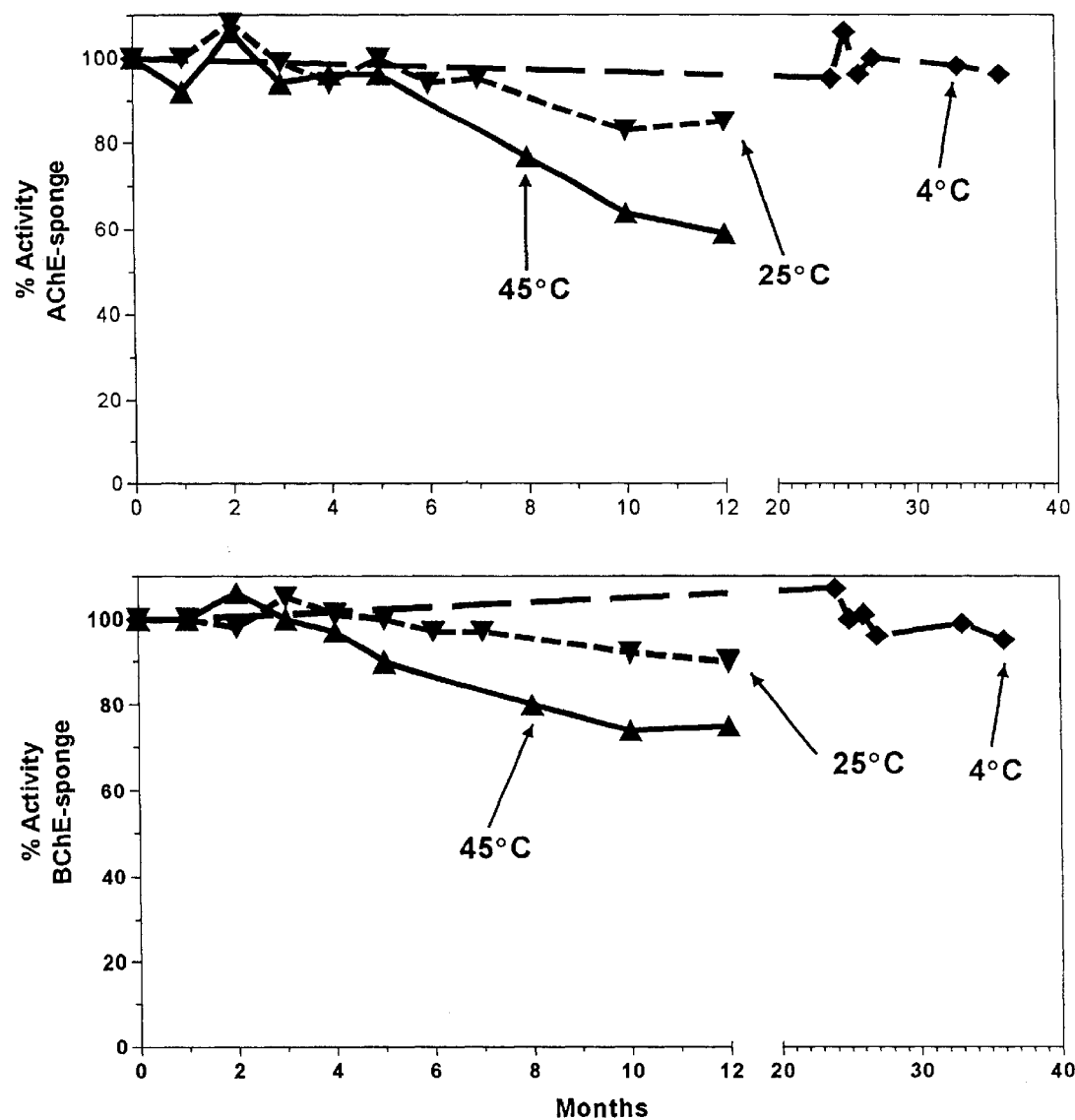
Stability of AChE (top) and BChE (bottom) sponges at various temperatures.

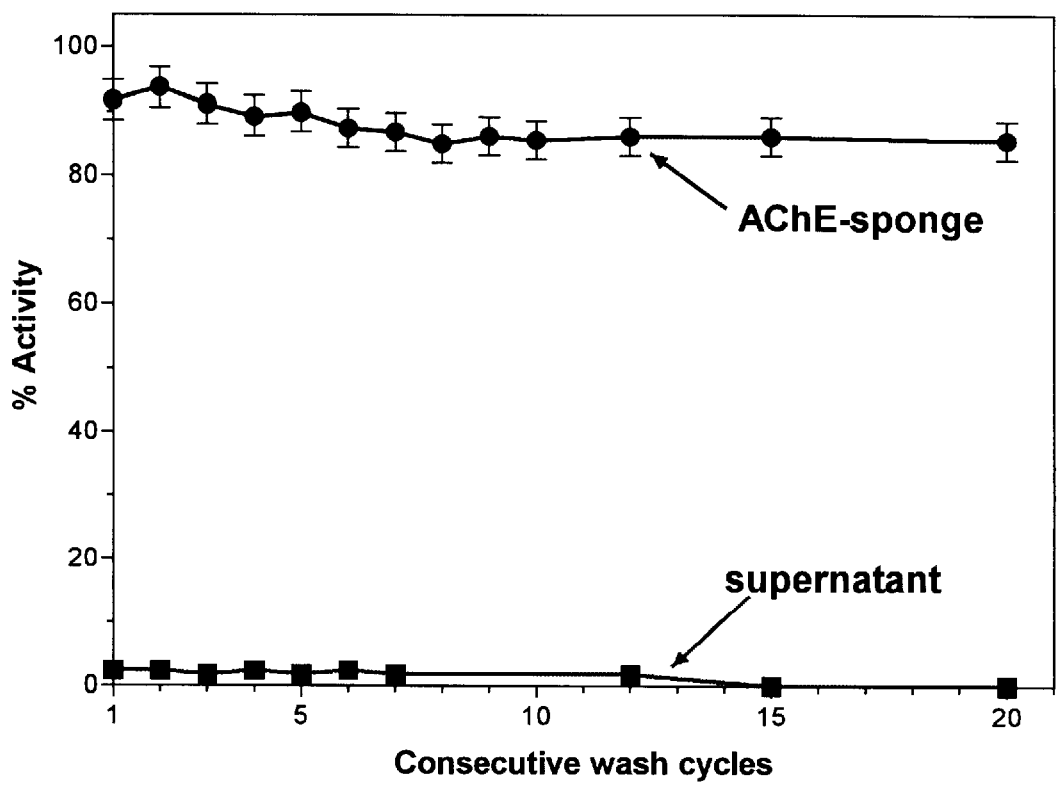
Figure 7. An AChE-sponge was alternately washed with phosphate buffer and assayed for activity. This procedure was carried out for three days. Similar results were observed for BChE-sponge.

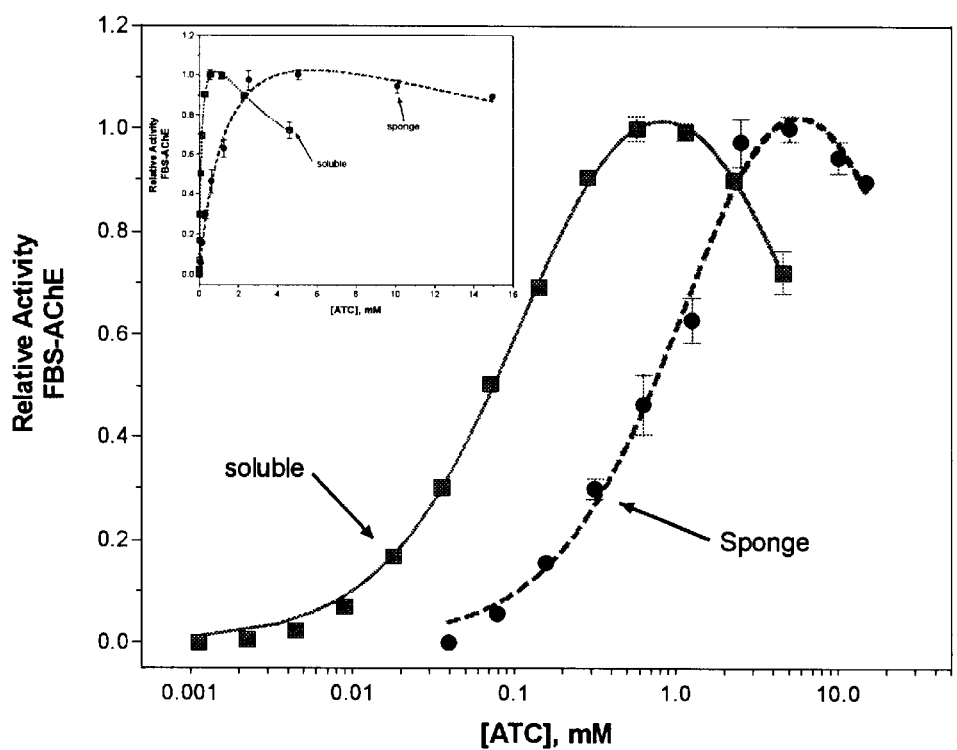
Figure 8. Substrate concentration dependent curve for soluble and polyurethane coupled AChE.

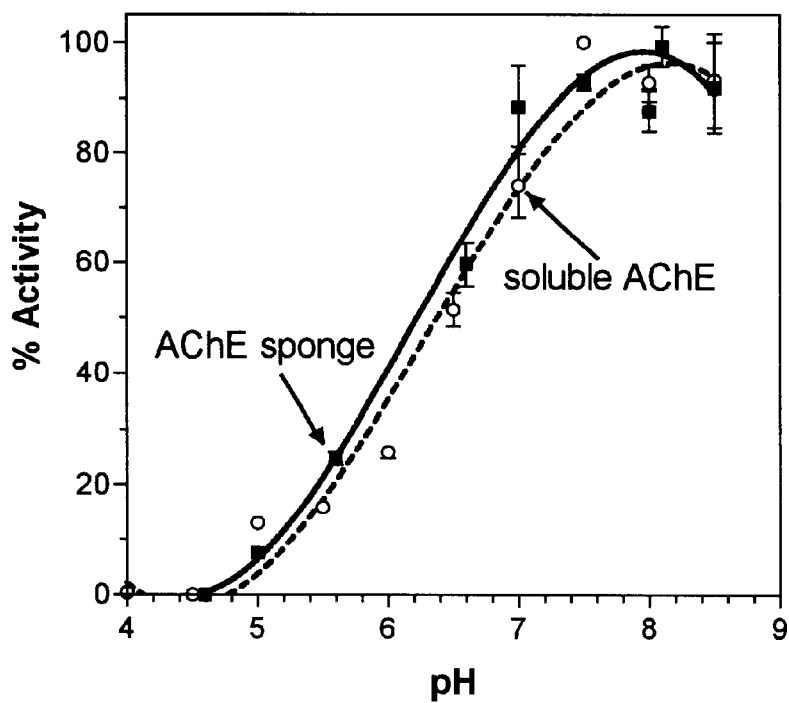
Figure 9. pH profile of soluble and immobilized acetylcholinesterase.

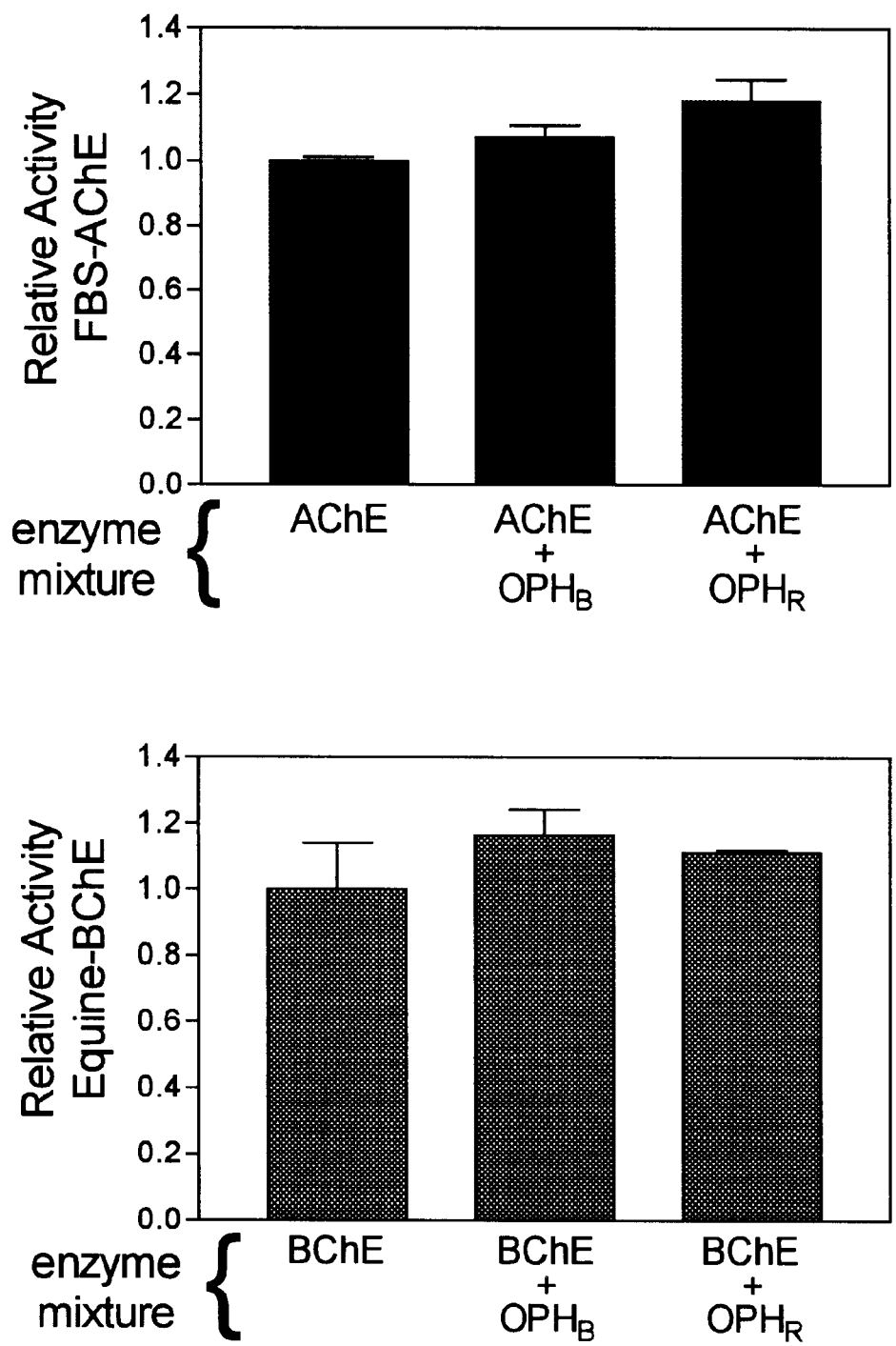
Figure 10.  Co-immobilization of ChEs and OP hydrolases.

Figure 11A shows a version of a manual mixing gun and Figure 11B shows a disposable mixing stator. Complete mixing of the enzyme in aqueous solution and the viscous prepolymer is accomplished in the stator. The product shown here for illustrative purposes is green, while the two starting components are yellow and blue.

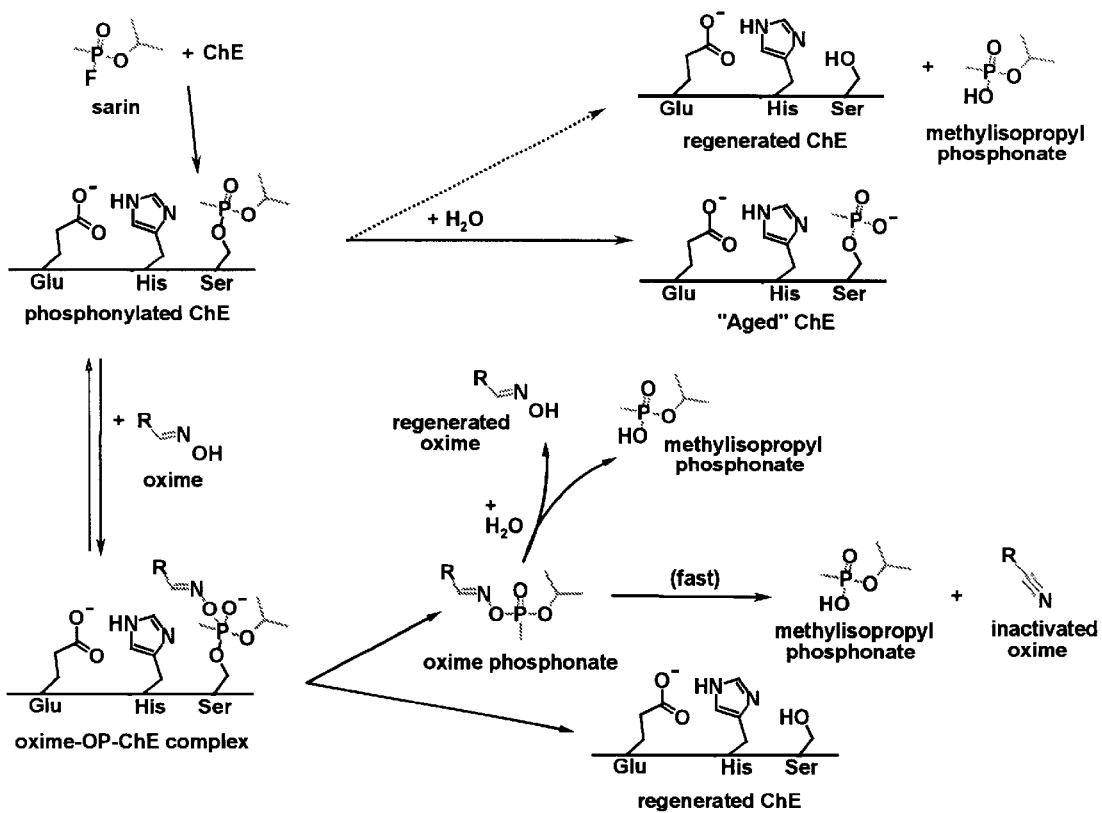
Figure 12. Reactivation of alkyphosphorylated ChE with oxime.

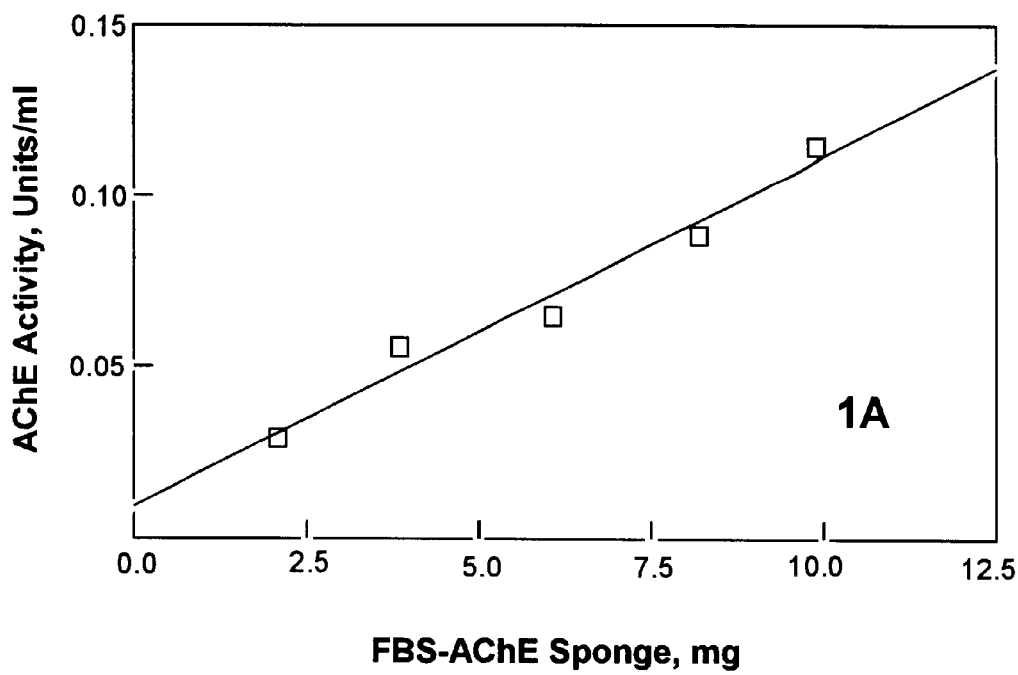
Fig. 13A.  Enzyme activity of immobilized FBS-AChE.
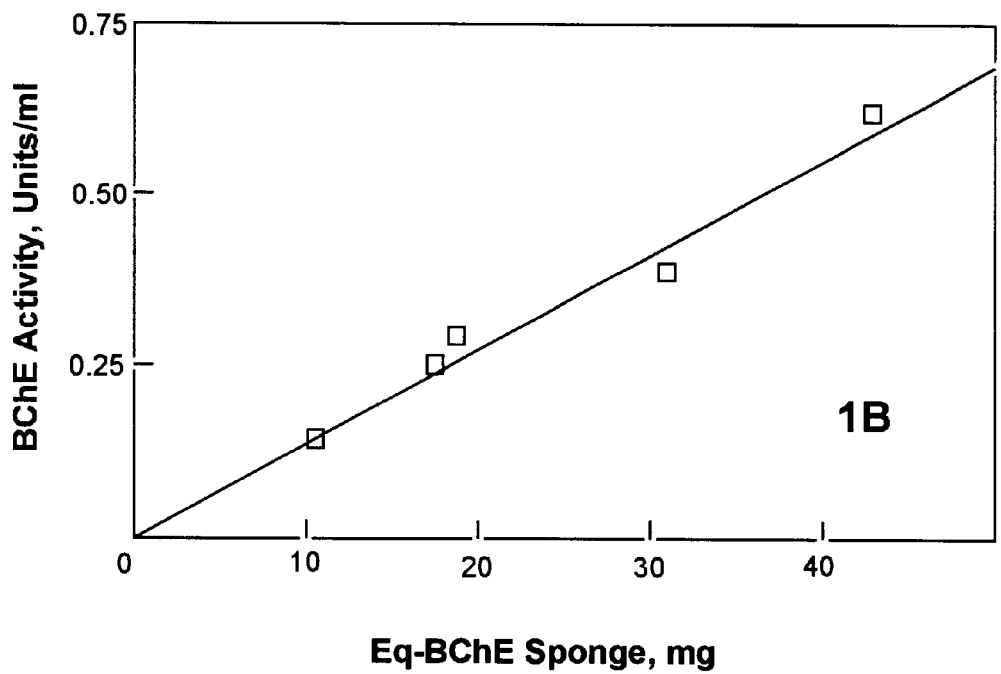
Fig. 13B.  Enzyme activity of immobilized Eq-BChE.

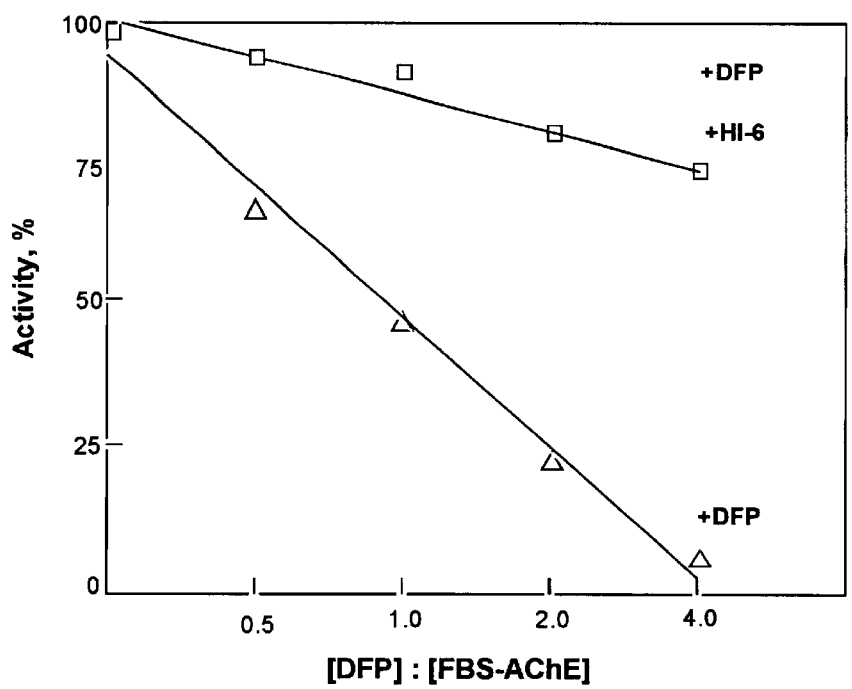
Figure 14. Inhibition of foam-immobilized FBS-AChE by DFP and reactivation by HI-6.

Figure 15. Inhibition of foam-immobilized Eq-BChE by DFP and reactivation by TMB4.

Figure A: shows protection afforded by sponge with tetraglyme additive.

Figure B: shows protection afforded by sponge with HI-6 additive.

Figure C: shows protection afforded by sponge with 2-PAM additive.

PREPARATION OF ENZYMATICALLY ACTIVE SPONGES OR FOAMS FOR DETOXIFICATION OF HAZARDOUS COMPOUNDS

RELATED APPLICATIONS

This application is based on Provisional Application No. 60/130,987, filed Apr. 26, 1999.

TECHNICAL FIELD

This invention relates to materials, compositions, kits and methods for neutralizing, detoxifying or decontaminating equipment and/or personnel exposed to organophosphorous and organosulfur compounds.

BACKGROUND OF THE INVENTION

Methods for decontamination, neutralization and removal of chemicals, such as organophosphorous and organosulfur (OP refers to both) compounds, herbicides and insecticides, are known in the art. However, the compositions and devices utilized in the prior art methods have undesirable properties, such as corrosiveness, flammability, toxicity, difficulty in making and storing, and limited shelf-life.

For example, DS2, a standard decontamination agent, comprises 70% diethylenetriamine, 28% ethylene glycol monomethyl ether, and 2% NaOH by weight. Although DS2 is effective, it is corrosive upon exposure to air. DS2 and any matter resulting from its use is classified and regulated as hazardous material. After an application, the DS2 must stand for 30 minutes before rinsing the treated area with water. Additionally, DS2 comprises a teratogen.

Some decontamination methods employ hypochlorite formulations which are corrosive and toxic and injure humans and sensitive tissues such as eyes. Other methods comprise incinerating the contaminated material and utilizing carbon filters to absorb the residual chemicals. Yet other methods utilize polymer beads or microemulsions which absorb the chemical and must be rinsed away. These methods are inherently dangerous, expensive and generate hazardous waste. Furthermore, as many of these compositions and compounds utilized degrade upon exposure to water and carbon dioxide, these compositions and compounds must be used the same day they are made.

Some in vivo methods employ cholinesterases in the presence of nucleophilic oximes to detoxify OP compounds. This enzyme bioscavenger approach is effective against a variety of OP compounds in rodents and nonhuman primates. For examples pretreatment of rhesus monkeys with fetal bovine serum acetylcholinesterase (FBS-AChE) or horse serum butyrylcholinesterase (Eq-BChE) confers protection against up to 5 $LD_{50}$ of soman, a highly toxic OP nerve agent. Although, the use of an enzyme as a single pretreatment drug for OP toxicity is sufficient to provide complete protection to an individual subject, a relatively large (stoichiometric) amount of the enzyme is required to neutralize the OP compound in vivo. Therefore, OP/enzyme stoichiometry is increased by combining enzyme pretreatment with oxime reactivation so that the catalytic activity of OP inhibited FBS-AChE is rapidly and continuously restored, and the OP compound is detoxified.

Clearly, a need for better methods and devices for neutralizing, detoxifying, decontaminating and cleaning materials, equipment and personnel exposed to OP compounds exists.

Recently, OP detoxifyng compounds, devices and methods thereof, which allow the safe, effective and convenient detoxification of highly toxic compounds not possible by the prior art, have been developed. These environmentally friendly compounds, devices and methods are disclosed hereinbelow.

SUMMARY OF THE INVENTION

The present invention provides materials, compositions, kits and methods for neutralizing, detoxifying or decontaminating equipment and/or personnel exposed to OP compounds.

In one embodiment, the invention relates to a material comprising a mixture of enzymes and substrates for the removal, decontamination and neutralization of OP compounds including those directed against humans. The mixture of enzymes utilized comprises cholinesterases (ChEs) and/or OP hydrolases and reactivators, such as oximes which includes mono-disquarternary oximes. The material may comprise a flexible or rigid porous support. The porous support may be a polyurethane matrix or equivalent.

For example, the porous support may be a flexible sponge-like substance or like material, wherein the enzymes are secured by immobilization. Depending on the polyurethane prepolymer or substrate utilized, porous supports of varying degrees of flexibility and porosity may be obtained. The porous support may be formed into various shapes, sizes and densities, depending on need and the shape of the mold. For example, the porous support may be formed into a typical household sponge or a towelette. The preferred dimensions of the sponge are 1"×2"×8" to 2"×4"×8". The preferred dimensions of the towelette are 4"×4"×0.25" to 4"×4"×0.03125" to 14"×14"×0.0625". However, during large-scale synthesis, the dimensions of the initial immobilized enzyme product might be large. For example, approximately 4 feet by 8 feet rolls could be produced and sized as appropriate and described above. The sponge-like support would be preferable for use on surfaces, including natural, synthetic and biological surfaces such as equipment, laboratory hardware, devices, skin and other delicate membranes, where decontamination of a rough or irregular surface is desired or where the prior art decontamination materials are incompatible with human tissue. For example, the materials may be used to clean and decontaminate wounds as it is non-toxic and the immobilized enzymes will not leach into a wound. Therefore, the sponges could be used to decontaminate civilians contaminated by a terrorist attack at a public event.

If an object and/or area to be neutralized or decontaminated comprises cracks, crevices, porous or uneven surfaces, a foam-like support is suitable. Application of small quantities may be done with a spray-bottle or spray can with an appropriate nozzle. Further, foam may be selected so that it can be dispensed into the opening of sensitive equipment or an orifice of a subject, such as the ear canal. If a large area is contaminated, an apparatus that dispenses a large quantity of foam may be utilized.

The foam-like support may dissipate after a period of time like shaving cream or it may cure into a stable and flexible sponge-like support. The dissipating foam may be applied on living subjects. The foam, which cures, may be applied around an object and contain the contamination within the foam. Once the foam cures, the object may be handled and moved without further exposure to the hazardous chemical.

When necessary, the material may also comprise a rigid and porous support. The rigid material can be ground into a powder and added to lotions, soaps and other liquids for application. Likewise, the flexible material, supra, may be appropriately treated to render it suitable for use in lotions, soaps and other liquids.

The material may also be in the form of a filter for neutralizing, detoxifying or decontaminating gases such as air. Additionally, the material may be in a form suitable for use as clothing or linings of clothing. Furthermore, the material may be used to decontaminate water by placing the material in water and then removing it from the water.

In another embodiment, the material can be color-coded according to the specific substance it may neutralize, detoxify or decontaminate. The color or color scheme could be selected to indicate enzymatic concentration, activity and/or remaining shelf-life or range thereof.

As disclosed herein, one of ordinary skill in the art will appreciate the various materials and their uses as contemplated by the inventors. All of these forms may be appropriately combined with carbon for further absorption of OP compounds. The carbon may be embedded or incorporated within the porous support of the material or the carbon may be a layer, filter or other to be used in conjunction with the material. Additionally, a slow release form, such as a dry capsule, pellet, liposome or other, of a reactivating compound and OP reacting compounds such as certain oximes like HI-6 and mono-bisquaternary oximes such as pralidoxime chloride (2-PAM) may be embedded or incorporated within the porous support of the material.

A preferred embodiment of the invention comprises a material wherein ACHE and/or BChE are simultaneously immobilized with OP hydrolases on or within the porous support during synthesis of the material. Preferably, the enzymes are immobilized through covalent linkages. The enzymes may be of prokaryotic or eukaryotic origin. The enzymes may be contained within the cell or cell free. The enzymes may be of recombinant origin. Other enzymes capable of hydrolyzing hazardous chemicals such as OP compounds may be employed, for example laccase. Additionally, other OP hydrolyzing enzymes would ensure rapid and complete destruction of any toxic intermediate (for example, phosphoryloximes) that might be generated during the decontaminaiton process. Likewise, enzymes such as triesterase may be used for the decontamination of pesticides in a similar manner as herein described. Preferred enzymes are those that may be reactivated.

The materials of the invention may be placed in containers to complete decontamination the OP compounds on the materials.

In another embodiment, the invention relates to the process of making a material, for the removal, decontamination or neutralization of hazardous chemicals such as OP compounds, comprising a mixture of enzymes immobilized on a porous support. In this embodiment, a mixture of enzymes and a prepolymer are gently and evenly mixed together with minimal degradation of the biotype component so that the resulting immobilized enzyme may effectively decontaminate, neutralize or detoxify an amount of an OP compound. The device utilized folds the components into one another. This is a low shear process. During synthesis of the material by prior art methods, for example a mixing drill, the enzymes utilized are subjected to fluid forces or shear stress. Use of a device that gently folds the components into one another greatly reduces these fluid forces or shear stress, and is the preferred device for enzymes, specifically enzymes that are sensitive to the high shear forces of the drill mixing device. Additionally use of additives such as surface-acting polymers, e.g. P-65, or low concentrations of glycerol protects against enzyme denaturation induced by shear forces, and modifies the final properties of the sponge to obtain the desired porosity and absorbent qualities.

In a preferred process of making the material, a two chamber apparatus is utilized. See FIG. 11A and B. One chamber contains a mixture of enzymes and the other chamber contains the prepolymer. The mixture of enzymes and the prepolymer are simultaneously extruded at a 1:1 ratio and mixed. Preferably, the mixture of enzymes and the prepolymer are rapidly and evenly extruded through a static mixing stator which gently and evenly mixes the enzymes and prepolymer. A preferred low shear device is a double chamber syringe and a static mixing stator typically used to mix viscous polyurethanes or epoxy glues. The size of the apparatus may vary depending on need. It may be pocketsize for use in the field by soldiers. Alternatively, the apparatus may be suitable for large-scale production and/or decontamination of a large objects or area. The low shear mixing device more than doubles the resultant ACHE or BChE immobilized enzyme activity when compared to an identical mixture prepared with the high shear device.

The invention further relates to various materials, methods and devices for reactivating the enzymatic activity of the material. These materials, methods and devices will allow a person to use the decontamination material of the invention for several separate uses and/or for a single and continuous use, which would normally require several decontamination materials but for reactivation of the enzymatic activity of the immobilized enzymes. Additionally, these materials, methods and devices allow for complete decontamination and/or neutralization of excess OP compounds absorbed by the porous support but did not react with the immobilized enzymes. These methods and reactivation materials employ substrates and/or oyimes, to reactivate the catalytic activity of the OP inhibited and immobilized enzymes.

The invention further relates to various materials and additives that are added to the embodiment to aid in the removal and decontamination of organophosphate from surfaces such as cracks, crevices, porous or uneven surfaces such as clothes and biological surfaces that readily absorb the organophosphates or pesticides such as skin. The additives are used in conjunction with the sponge material and may be incorporated within the porous support of the material. The additives may be in a dry or liquid form, and may be organophosphate solubilizing compounds such as triacetin or tetraglyme, or oximes, which both aid in decontaminating and reactivating enzymes.

Another embodiment of the invention relates to a variety of kits. Along with the sponge containing a plurality of enzymes needed for the decontamination of organophosphorous and/or sulfur compounds the kit may include materials which would facilitate or be deemed necessary for the decontamination process. Kits may also include polymeric materials and enzymes if the foam is transient in nature, e.g. the prepolymer, a stable enzyme mixture and a low shear apparatus for making an organophosphorous and/or organosulfur decontamination foam. The kits may contain items to facilitate the use of the device, e.g. instructions, containers, test tubes, etc.

DESCRIPTION OF THE DRAWINGS

This invention is further understood by reference to the drawings wherein:

FIG. 1A illustrates the modeled surfaces of acetylcholinesterase, butyrycholinesterase and phosphotriesterase.

FIG. 1B illustrates the modeled surface of laccase.

FIG. 2 shows a cured material.

FIG. 3 schematically illustrates the specific reaction of the enzymes with prepolymer and the product polyurethane crosslinked ChE.

FIG. 4 shows the linear correlation between the amount of BChE added during synthesis of the material and the amount of BCHE in the final material.

FIG. 5 shows the increasing amounts of BSA added during synthesis to a constant amount of ACHE and TDI polymer.

FIGS. 6A and B illustrates that the materials maintained enzymatic stability for more than 12 months at 25° and 45° C. and 3 years at 4° C. for AChE (A) and BChE(B).

FIG. 7 shows that the material maintained enzymatic activity after consecutive washes.

FIG. 8 shows a substrate concentration dependent curve for soluble and polyurethane coupled AChE.

FIG. 9 illustrates the pH range of soluble and immobilized ACHE.

FIG. 10 shows the relative activities of co-immobilized ChEs and OPHs.

FIG. 12 illustrates how oximes reactivate alkylphosphorylated ChE.

FIG. 13A illustrates the enzyme activity of immobilized FBS-AChE. FIG. 13B illustrates the enzyme activity of immobilized Eq-BChE.

FIG. 14 represents inhibition of foam-immobilized FBS-AChE by DFP and reactivation by HI-6.

FIG. 15 represents inhibition of foam-immobilized Eq-BChE by DFP and reactivation by TMB4.

DETAILED DESCRIPTION OF THE INVENTION

Figure 11A:
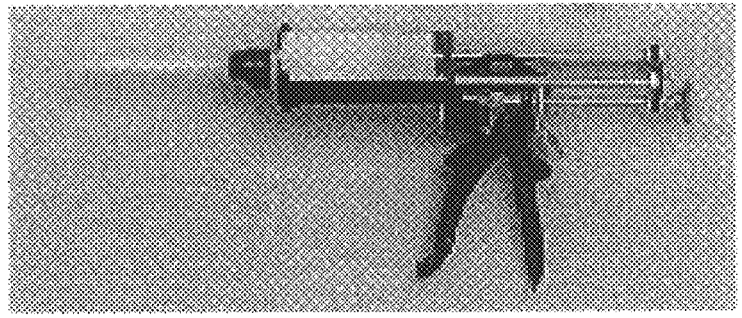
FIGS. 11A and B shows a version of a manual mixing gun and a disposable mixing stator.

Enzymes have been incorporated in hypo-based urethane foam during polymer synthesis. See U.S. Pat. No. 4,342,834. Hypoprepolymer is synthesized from a reaction of polyether (or polyester) polyol with isocyanates in the presence of cross-linking agents. See Havens, P. L., et al., *Ind Eng Chem Res* (1993) 32:2254–2258; U.S. Pat. No. 4,137,200; LeJeune, K. E., et al., *Biotechnology and Bioengineering* (1999) 20;62(6):659–665. Synthesis is initiated by bringing water molecules into contact with isocyanate groups present within the polyurethane prepolymer.

A two-step procedure occurs from this point. Isocyanates react with water to form an unstable carbonic acid, which in turn degrades to an amine yielding $CO_2$ that gives the porous support lift and enables it to rise. The amines readily react with isocyanate groups, leading to production of urea type linkages. Since the enzyme contains multiple functional groups, such as amines and hydroxyls that can react with isocyanates, the enzyme becomes an integral part of the porous support during synthesis. Significant quantities of enzyme can link to the porous support without disrupting the progress of polymer synthesis. The reaction occurring during the polymer synthesis is shown below.

1. $CO_2$ Evolution:

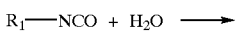
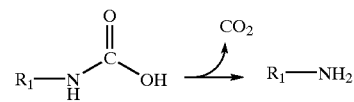

2. Urea Linkage:

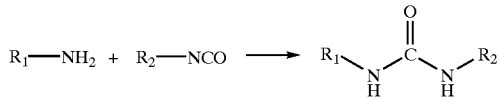

3. Amine Group Enzyme Immobilization:

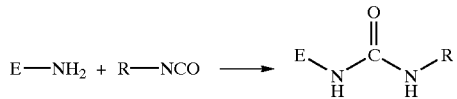

4. Hydroxyl Group Enzyme Immobilization:

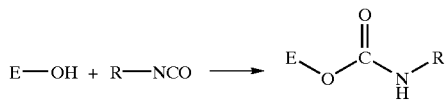

The following list of enzymes and chemicals are examples of those suitable for use in the instant invention:

Acetylcholinesterase (AChE);
Butyrylcholinesterase (BChE);
Pseudocholinesterase;
Organophosphate hydrolases (OPH);
Phosphotriesterase;
*Pseudomonas diminuta* bacterial OPH (paraoxonase);
Laccases;
Organophosphate acid anhydrase (OPAA)
Pralidoxime chloride (2-PAM);
7-(methoxyphosphinyloxy)-1-methylquinolium iodide (MEPQ);
Diisopropyl fluorophosphate (DFP);
Acetylthiocholine iodide (ATC);
S-butyrylthiocholine iodide (BTC);
5,5'-dithio-bis(2-nitrobenzoic acid) (DTNB);
N,N'-trimethylene bis(pyridinium-4-aldoxime) dibromide (TMB4); and
1-(2-hydroxyiminomethyl-1-pyridinium)-1-(4-carboxyaminopyridinium)-dimethylether hydrochloride (HI-6).

The following examples are intended to illustrate but not to limit the invention.

EXAMPLE 1

Determination of Possible Enzyme Interference

As polyether prepolymer derived from tolyl diisocyanate (TDI), reacts most favorably with free aliphatic amines such as lysine and arginine present on the surface of the ChEs (or any protein) to become a permanent cross-linked part of the material, computer aided molecular modeling of the enzymes was performed to highlight the available amino groups on the surface of each enzyme, and to determine whether the coupling of these groups to a porous support would interfere with enzymatic function. This may be performed on every enzyme for which its crystal structure is known, or enzymes which may be modeled by homology.

FIG. 1A illustrates the modeled surfaces of acetylcholinesterase, butyrycholinesterase and phosphotriesterase and shows the lysine and arginine residues on the surface of the ChEs which are available for coupling to the prepolymer. This was generated by Insight II, molecular modeling software, by Biosym Technologies. Based on the molecular modeling, there are at least one lysine and 29 arginine water-accessible residues on the surface of FBS-ACHE to couple to the porous support, while 26 lysine and 26 arginine residues were modeled for equine-BChE. The majority of the lysine and arginine residues were found on the backside of the ChEs, and only a few are found on the side of the enzyme where the catalytic site gorge is located. The rim and the catalytic site gorge opening of both AChE and BChE appeared to be essentially devoid of lysine and arginine. Therefore, coupling these enzymes to the porous support should have minimal effect on the entrance of substrate, inhibitors such as OPs, or reactivators such as oximes which includes mono-disquarternary oximes, release of products of catalysis to and from the active site, and the kinetic rates of the enzymes. Similarly, a model of the surface of laccase (FIG. 1B) is shown with available residues to couple covalently to the prepolymer.

EXAMPLE 2

Synthesis of an Enzyme Bound Polyurethane Material

A typical synthesis of the material comprises mixing enzymes in phosphate buffer containing 1% (final concentration) surfactant with prepolymer. Polyether prepolymer derived from tolyl diisocyanate (TDI), Hypol prepolymer TDI 3000 (Hampshire Chemical, Lexington, Mass.), and Pluronic P-65 surfactant (BASF Specialty Chemicals, Parsippany, N.J.) were used. The 2-phase system is mixed and placed into a suitable mold and left to cure. FIG. 2 shows a cured material which comprises a sponge-like support.

FIG. 3 schematically illustrates the specific reaction of the enzymes with prepolymer. Synthesis begins when $H_2O$ molecules react with the isocyanate groups present within the polyurethane prepolymer. Isocyanate reacts with the water to form an unstable carbonic acid, which degrades to an amine yielding $CO_2$. The $CO_2$ causes the polymer to rise and become porous, and simultaneously the amines readily react with the isocyanate groups leading to urea linkages. While the amino groups are the preferred reaction site between the enzyme(s) and the prepolymer, hydroxyl (OH) groups are also available to interact within the reaction buffer, e.g. $H_2O$ and on the enzyme(s).

Since the ChE contains amines that are on the surface and available to react with the isocyanate groups, they can become an integral part of the polyurethane support during synthesis. There is no significant entrapment of the enzyme in the material as found with cyclodextrins, or physical adsorption of the enzymes, as observed with activated carbon. The inclusion of a surfactant such as Pluronic P-65 at about 1% final concentration controls the final structure and absorption potential of the material.

To create a material comprising a porous polyurethane support, approximately 30 mL of 50 mM phosphate buffer, pH 8.0, containing P-65 surfactant buffer, was placed in a 600 mL plastic beaker. 3 to 5 mL of either purified FBS-AChE (7500 units) or purified Eq-BChE (5000 units) was added, followed by approximately 40 gm of Hypo 3000 prepolymer (tolyl diisocyanate). The two-phase system was mixed and the material was allowed to expand for 10 min, extruded from the container. The material was washed thoroughly with 50 mM phosphate buffer, pH 8.0, dried and stored in a zippered bag at 4° C. for future use.

EXAMPLE 3

Characteristics of Synthesized Material

Approximately 20–90% of the enzymes were covalently linked to the porous support through free amino- or hydroxyl groups. This was determined by the presence of enzyme in first and second washes of the material.

Since the enzymes can be attached at multiple points, they become a part of the cross-linked polymer support. The cross-linked polymer support imparts considerable stability to the bound enzymes. A large quantity of enzyme can be incorporated into a small polyurethane support, thereby rendering the cross-linked polymer support a highly effective material for decontamination.

A. Enzymatic Activity.

Five samples of materials containing FBS-ACHE and five samples of materials containing Eq-BCHE, ranging in weight from I to 40 mg, were suspended in 2.8 mL of 50 mM phosphate buffer, pH 8.0, and assayed using the method of Eliman. See Ellman, G. L., et al., (1961) *Biochem Pharmacol.* 7:88–95. A linear correlation was found between the weight of the sponge and enzyme activity for both FBS-ACHE and Eq-BChE immobilizations. See FIGS. 13A and B. The linear correlation between the weight of the material and enzyme activity indicates a uniform immobilization of ACHE or BCHE throughout the material.

The material was washed with either 50 mM phosphate buffer, distilled water, or 10 mM ammonium bicarbonate without affecting substrate hydrolysis. Therefore, the mixing of prepolymer, surfactant, and enzyme in situ at 22° C. yields a useful and effective material retaining about 50% of the original activity of soluble ChE.

B. Protein Loading Capacity.

The material has a significantly higher loading capacity for ChEs such as BCHE or ACHE. The final activity of the BChE immobilized in the material could be increased by adding larger quantities of enzyme during synthesis. See FIG. 4. When nonspecific protein (bovine serum albumin, BSA) was added to a constant amount of purified ACHE, there was no reduction in ChE activity. See FIG. 5. Thus, higher potency materials may be synthesized with additional proteins, enzymes and other ChEs. Additionally, materials effective against a diverse array of OP compounds may be readily synthesized by with combinations of multiple enzymes or a plurality of enzymes.

C. Enzymatic Stability.

As illustrated by FIG. 6, the immobilized ChE and OP hydrolase maintained enzymatic stability for more than 12 months at 25° C. and 45° C., respectively. If the material is frozen in liquid nitrogen, most of the original activity remains. TDI imparts remarkable stability to the immobilized ChE; about 50% of the original activity of the immobilized ACHE and 20% of the activity of the immobilized BCHE remained after 16 hours at 80° C., conditions under which the soluble enzymes would exhibit no activity. The ChE materials can be exhaustively dried under vacuum at 22° C. and then rehydrated without loss of enzyme activity.

When AChE or BChE materials were exhaustively washed and assayed for activity, the wash and assay cycle repeated more than twenty times over three days, no decrease in activity occurred. See FIG. 7. This indicates that the material may be used repeatedly.

These results also demonstrate that the ChEs are covalently cross-linked in the porous support and that the ChEs will not leach out to skin, water, or equipment. Therefore, once the immobilized enzymes bind an OP compound the OP is removed from the surface requiring decontamination.

D. Kinetic Constants.

The number of active sites of either the immobilized or soluble ChEs was determined by titration with the organophosphorous compound MEPQ, 7-(methylethoxyphosphinyloxy)-1-methylquinolinium iodide. The bimolecular rate constants for the inhibition of AChE material and BCHE material and the respective soluble enzymes by MEPQ at 25° C. showed that there was no significant difference between the soluble and covalently bound enzymes. See Table 1.

TABLE 1

Time-Dependent Inhibition of ChEs by MEPQ

| ChE | Enzyme Form | Bimolecular rate constant $(M^{-1} min^{-1}) \pm SD$ |
|---|---|---|
| FBS-AChE | soluble | $1.59 \pm 0.52 \times 10^8$ |
|  | coupled to sponge | $1.00 \pm 0.28 \times 10^8$ |
| Equine-BChE | soluble | $4.15 \pm 0.78 \times 10^7$ |
|  | coupled to sponge | $4.21 \pm 2.00 \times 10^7$ |

These results demonstrate that the immobilized and soluble forms of ChEs interact with the OP compounds similarly. Therefore, enzymatic activity assays which are generally available and known in the art may be used.

An initial rates method using a modified Eliman's assay was used to determine the parameters $K_m$, $k_{cat}$, and $k_{cat}/K_m$ for immobilized and soluble AChE and BChE. The number of active sites of either the coupled or soluble ChEs was determined by titration with MEPQ. As shown in Table 2 and FIG. 8 for ACHE, the $K_m$ values for the immobilized ChEs were about 10-fold greater than the corresponding soluble enzymes, and the $k_{cat}$ values were less dramatically affected. The combined effects on affinity for substrate and kcat resulted in approximately a 20 to 50-fold decrease in acylation ($k_{cat}/K_m$). Interestingly, while soluble BChE lacked substrate inhibition, immobilized BChE yielded substrate inhibition. These results suggest that covalent binding of surface residues of ChEs to the porous support changed some properties of the active site region of the bound enzymes directly or indirectly.

TABLE 2

Kinetic parameters for soluble and polyurethane coupled ChEs.

| Enzyme | Form | Substrate inhibition | $K_m$ (mM) | $K_{ss}$ (mM) | B | $K_{cat}$ (min$^{-1}$) | $K_{cat}/K_m$ (M$^{-1}$ min$^{-1}$) |
|---|---|---|---|---|---|---|---|
| FBS-AChE | Soluble | yes | 0.119 | 18 | — | $2.8 \times 10^5$ | $2.5 \times 10^9$ |
|  | immobilized | yes | 1.090 | 22 | — | $5.9 \times 10^4$ | $5.4 \times 10^7$ |
| Equine-BChE | Soluble | no | 0.127 | 1.5 | 1.8 | $3.1 \times 10^4$ | $2.4 \times 10^8$ |
|  | immobilized | yes | 1.200 | 16 | — | $1.8 \times 10^4$ | $1.5 \times 10^7$ |

Determined in 50 mM phosphate, pH 8 at 25° C. using an initial rates method.
Calculated from $V_{max}$ and the active site concentration of ChE that was determined by MEPQ titration.
Values were calculated[2] using modified Haldane equations, and the special case where b = 0. The best fit between the two was determined using an F test, where significance was defined as $p < 0.05$.

Generally, immobilized cholinesterases or OP hydrolyzing enzymes exhibit between the same to 10 fold greater $K_m$ values than the corresponding soluble enzymes. In addition to the cholinesterases, OPH (derived from *Pseudomonas diminuta*, FIG. 19A) shows about a 10-fold increase in $K_m$ because a shift to the right is also observed in the immobilized (sponge) form when determined using the substrate paraoxon. On the other hand, OPAA (derived from Alteromonas, FIG. 19B), shows little change in $K_m$ for the substrate paraoxon.

E. pH of Soluble and Immobilized Enzymes.

The pH profiles of immobilized and soluble ACHE are identical and the enzymes exhibit activity throughout the broad pH range of 7–8.5. See FIG. 9. Since the pH profiles of soluble cholinesterases and OP hydrolases have optimal activities in this same pH range, the materials may be optimized and diversified by employing a plurality of these multiple enzymes immobilized on or within a porous support.

EXAMPLE 4

Immobilization of a Plurality of Enzymes

ChEs were co-immobilized with bacterial OP hydrolase (OPH$_B$) and/or rabbit serum OP hydrolase (OPHR). There was no reduction in the enzymatic activities of AChE or BChE co-immobilized with OPH as compared to the enzymatic activities of each of these enzymes individually immobilized. See FIG. 10. Additionally, there was no reduction in the enzymatic activity of co-immobilized OPH. Therefore, a plurality of enzymes, which each enzyme differentially reacts with various OP compounds, may be selected and utilized in a material to create a decontamination material effective against a wide range of OP compounds.

EXAMPLE 5

Rapid Mixing Synthesis

Figure 11B:
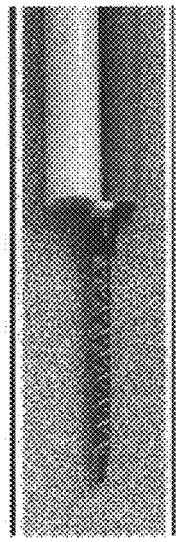
Figure 16:
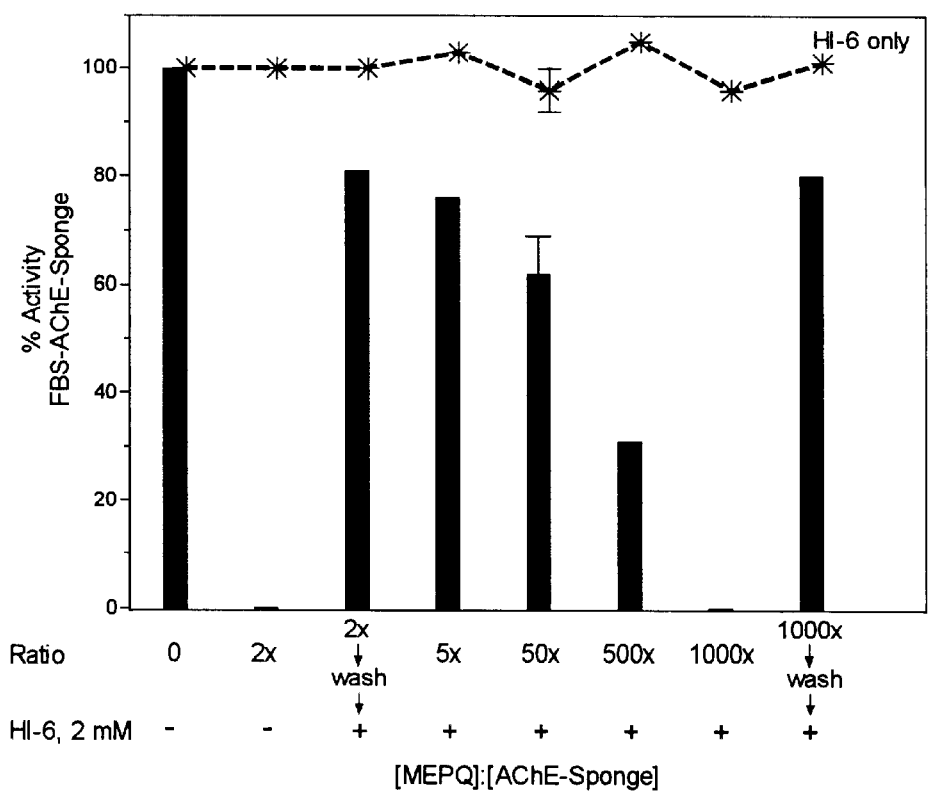
FIG. 16 shows restoration of the original sponge activity with HM-6.
Figure 17:
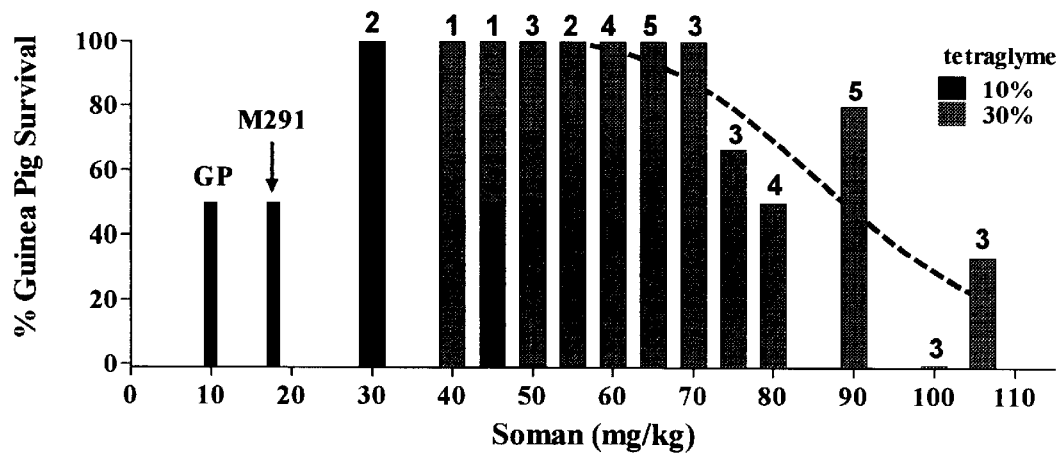
FIG. 17 (A, B and C) shows the protection afforded by sponge with various additives, i.e. tetraglyme (A), HI-6 (B) and 2-PAM (C).
Figure 17:
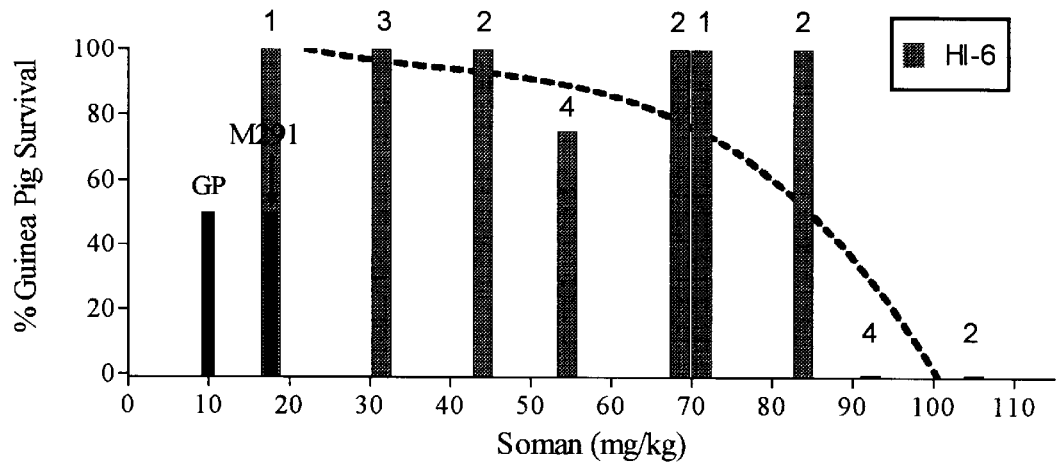
Figure 17:
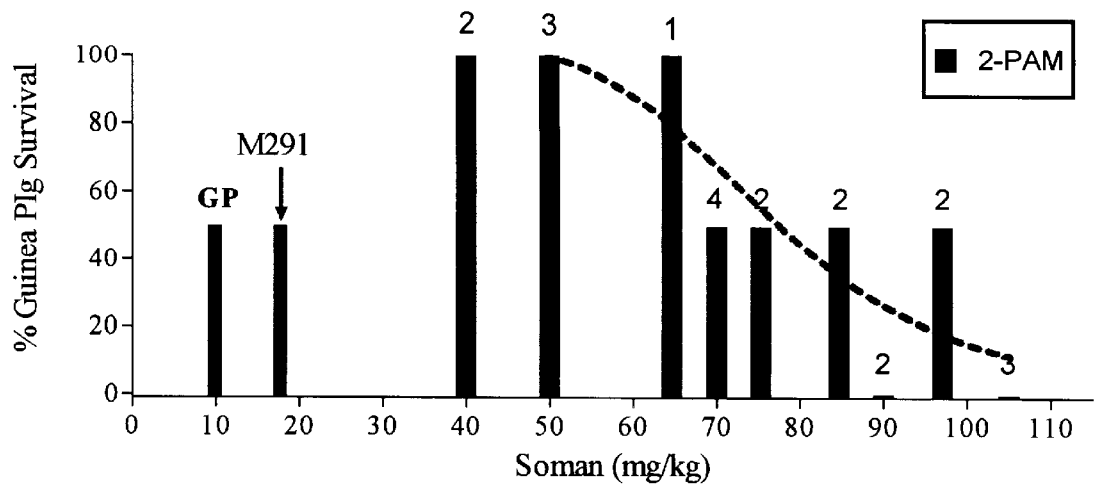
Figure 18:
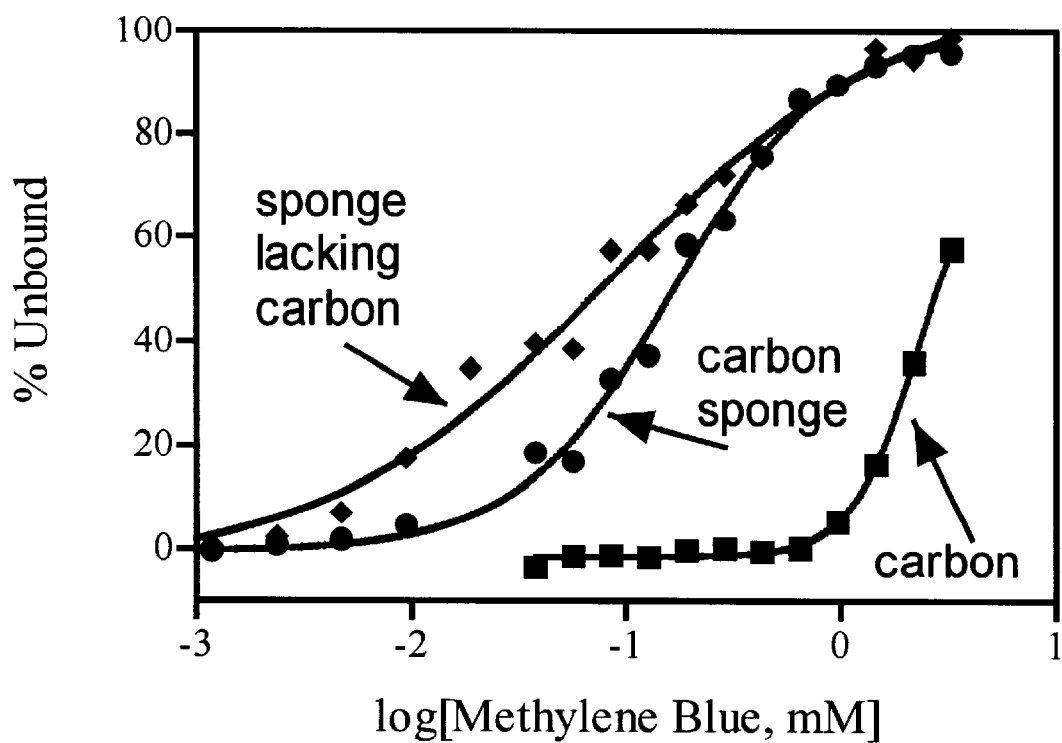
FIG. 18 shows the capacity of the resulting carbon sponge for binding methylene blue.

By utilizing a method of syntheses modified from the adhesive industry (CPA, Greenville, R.I. 02828) shear forces which decrease enzymatic activity are reduced. See FIG. 11. In this method, the enzyme is not in an organic buffer as required in some immobilization techniques. This results in less air-induced shearing, thereby maintaining enzymatic activity. This method is also simple to conduct, rapid and reproducible. The low shear mixing device more than doubles the resultant AChE and/or BChE immobilized enzyme activity when compared to an identical mixture prepared with the high shear device such as a mixing drill. See Table 3.

TABLE 3

| Technique | AChE Activity U/mg |
|---|---|
| High shear mixing drill | 0.100 |
| Low shear 2-chamber device | 0.270 |

EXAMPLE 6

Inhibition of Immobilized FBS-BChE with DFP and Reactivation With HI-6

100 mg samples of immobilized FBS-AChE were incubated with varying concentrations of DFP in 2 mL of 50 mM phosphate buffer, pH 8.0, for 1 hour at 25° C. In parallel experiments, 1 mM HI-6 was added to the same amount of material and DFP. Residual DFP in the samples was measured by adding a 0.5 mL aliquot of the reaction mixture to 0.5 mL of a fresh 1 U/mL solution of FBS-AChE, incubating for 1 hour, and assaying 10 T1 aliquots using the Ellman procedure. The results are shown in FIG. 14.

The inhibition of FBS-AChE activity by DFP was proportional to the stoichiometric amount of DFP added to the foam suspended in buffer. The presence of 1 mM HI-6 nearly completely prevented enzyme inhibition by DFP. This indicates that immobilized FBS-AChE may be repeatedly reused after reactivating the enzyme with an oxime solution such as HI-6.

FIG. 12 illustrates how oximes may reactivate alkylphosphorylated ChE activity.

EXAMPLE 7

Inhibition of Immobilized Eq-BChE With DFP and Reactivation With TMB4

50 mg samples of immobilized Eq-BChE were incubated with varying concentrations of DFP in 2 mL of 50 mM phosphate buffer, pH 8.0, for 18 hours at 25° C. In parallel experiments, 1 mM TMB4 was added to the same amount of material and DFP. Residual DFP in the samples was determined by adding a 0.5 mL aliquot of the reaction mixture to 0.5 mL of a fresh 1 U/mL solution of Eq-BChE, incubating for 1 hour, and assaying 10T1 aliquots using the Eliman procedure.

TMB4 was used as a reactivator instead of HI-6, since TMB4 is a more efficient reactivator of inhibited Eq-BChE than is HI-6. These results are shown in FIG. 15. As in Example 6, the foam-bound Eq-BChE may be repeatedly reused after reactivating the enzyme with an oxime solution such as TMB4.

EXAMPLE 8

Inhibition of Immobilized ACHE With the Organophosphate MEPQ and Detoxification of the MEPQ and Reactivation of the Immobilized Enzyme in the Presence of HI-6

50 mg samples of immobilized acetylcholinesterase were incubated with varying concentrations of MEPQ in 2 mL of 50 mM phosphate buffer, pH 8.0 at 25° C. for 1 hr. In the absence of oxime HI-6, the sponge soaks up the MEPQ and is inactivated. Addition of HI-6 reactivates the sponge's activity, and the MEPQ is detoxified, and most of the original activity of the sponge returns. Only at very high ratios of organophosphate (1000-fold molar excess) is the process of binding, reactivation, and detoxification not complete. However, fresh HI-6 can restore most of the original activity once again. See FIG. 16.

EXAMPLE 9

Additives to the Sponge to Improve Decontamination of Soman (GD) Contaminated Skin of Guinea Pigs Sponges approximately 1½×2½×¼" (H×L×D) contained 9.0 mL of additive and a second sponge contained 4.5 mL of additive. Each guinea pig was wiped with the first sponge and then the second sponge after soman (GD) exposure. Survival of the guinea pigs was determined after 24 hours, and the protective ratio determined. The protective ratio is the ratio of the $LD_{50}$ of the sponge containing an additive to the $LD_{50}$ of soman in the absence of sponge. Thus, the higher the $LD_{50}$, then the higher the protective ratio and the more effective the sponge combination is for decontamination of guinea pig skin and protecting the animal from the organophosphate. The sponge was compared to the M291 kit (available from Truetech, Inc.), the currently used decontamination kit fielded by the US Army. As shown in the table, the sponges provide 4 to 5-fold better protection than the M291 kit.

FIG. 17A shows the protection afforded by tetraglyme; FIG. 17B the protection afforded by HI-6, and FIG. 17C the protection afforded by 2-PAM. The number on the top of each bar shows the number of guinea pigs evaluated at the indicated dose of soman (GD). For reference, the $LD_{50}$ of soman on guinea pigs without any effort to decontaminate is shown by the label "GP", while the protection offered by the M291 kit is shown by "M291". Other additives to the sponge such as triacetin also afforded some additional protection compared to the M291 kit.

| Additive to sponge | $LD_{50}$ | Protective Ratio |
|---|---|---|
| HI-6 (oxime, 50 mM) | 79 | 8.0 |
| 2-PAM (oxime, 50 mM) | 76 | 7.7 |
| Tetraglyme (30%) | 88 | 8.9 |
| | Reference values | |
| M291 decon kit | 17.7 | 1.8 |
| Soman alone | 9.9 | — |

EXAMPLE 10

Activated Carbon Containing Sponge 0.5–1 grams of activated carbon was added to about 4 mL of the prepolymer prior to mixing with acetylcholinesterase (5 mL of Electric eel, in 50 mM pH 8.0 phosphate buffer with 1% Pluronic P-65) to produce an acetylcholinesterase immobilized carbon sponge. The addition of carbon did not interfere with the immobilization of the enzyme, as shown in the table. The capacity of the resulting carbon sponge for binding methylene blue (an colorimetric indicator for 1) activated carbon or resin) is illustrated in the FIG. 18. Therefore, comparison of the sponge with activated carbon to the sponge lacking activated carbon demonstrates that it can bind about 2-fold more methylene blue at less than saturating concentrations.

Activities of Sponges and Activated Carbon

| Type of Sponge | Relative Activity (% control in absence of carbon) | Relative Activity to absorb methylene blue |
| --- | --- | --- |
| Electric eel AChE sponge | 100% | 1X |
| Electric eel AChE sponge with Activated Carbon | 108% | 2X |
| Activated Carbon not in the sponge | — | 13X |

Incorporation by Reference

To the extent necessary to understand or complete the disclosure of the present invention, all publications, patents, and patent applications mentioned herein are expressly incorporated by reference therein to the same extent as though each were individually so incorporated.

What is claimed is:

1. A method of making an enzymatically active reusable polymeric sponge or foam, capable of regeneration with oximes, for the detoxification of a hazardous compound comprising immobilizing a plurality of enzymes on or within the sponge or foam by mixing the plurality of enzymes with a polyurethane prepolymer in an apparatus having a static mixing stator connected to both first chamber and a second chamber, wherein the first chamber contains a mixture of the plurality of enzymes and the second chamber contains the polyurethane prepolymer, and equal parts of the mixture of the plurality of enzymes and the polyurethane prepolymer are passed from the first and second chambers into the static mixing stator where the enzymes and prepolymer are mixed under low shear conditions while being rapidly and evenly extruded through the static mixing stator to form said sponge or foam, said plurality of enzymes capable of detoxifying organophosphorous and/or organosulfur compounds, wherein said plurality of enzymes comprises at least one enzyme selected from the group consisting of: acetylcholinesterase (AchE), butylcholinesterase (BchE), triesterase, pseudocholinesterase, organophosphate hydrase (OPH), phosphotriesterase, paraoxonase and organophosphorus and organosulfur (OP) hydrolyzing enzymes.

2. The method of claim 1 wherein said polyurethane prepolymner comprises a diisocyanate.

3. The method of claim 2 wherein the diisocyanate is tolyl diisocyanate.

4. The enzymatically active reusable polymeric sponge or foam for the detoxification of a hazardous compound made by the method of claim 1.

5. A method of reactivating said polymeric sponge or foam of claim 4 by contacting the sponge or foam with at least one compound selected from the group consisting of 1-(2-hydroxy iminomethyl-1-pyridium-1-(4-carboxyaminopyrididinium)-dimethyl ether hydrochloride (HI-6), N,N-trimethylene bispyridinium-4-aldoximme dibromide (TMB4), and mono-bisquarternary oximes.

6. A method for treating a contaminated surface comprising contacting the surface with the reusable sponge or foam of claim 4 to detoxify organophosphorous and/or organosulfur compounds present on the surface.

7. The method of claim 6 further comprising contacting the sponge or foam with an oxime.

8. The method of claim 7 wherein the oxime is 1-(2-hydroxy iminomethyl-1-pyridium-1-(4-carboxyaminopyrididinium)-dimethyl ether hydrochloride (HI-6) or pralidoximine chloride (2-PAM).

9. The method of claim 6, wherein the sponge or foam additionally contains activated carbon and/or resin.

10. The method of claim 9, wherein the sponge or foam contains activated carbon.

11. A kit for the detoxification of a hazardous chemical comprising a reusable a polymeric sponge or foam of claim 4 and a compound for the reactivation of the plurality of enzymes.

* * * * *

UNITED STATES PATENT AND TRADEMARK OFFICE
CERTIFICATE OF CORRECTION

PATENT NO.      : 6,642,037 B2
DATED           : November 4, 2003
INVENTOR(S)     : Richard K. Gordon et al.

It is certified that error appears in the above-identified patent and that said Letters Patent is hereby corrected as shown below:

<u>Title page,</u>
Item [75], Inventors, should read as follows:
-- [75]  Inventors:  Richard K Gordon, Potomac, MD (US)
                    Bhupendra P. Doctor, Potomac, MD (US)
                    Shawn R. Feaster, Damascus, MD (US)
                    Donald Maxwell, Baltimore, MD (US)
                    Michelle Ross, Edgewood, MD (US)
                    David Lenz, Bel Air, MD (US) --

Signed and Sealed this

Twenty-second Day of June, 2004

JON W. DUDAS
*Acting Director of the United States Patent and Trademark Office*